(12) United States Patent
Ragaglia et al.

(10) Patent No.: US 6,653,143 B2
(45) Date of Patent: Nov. 25, 2003

(54) PROCESS AND DEVICE OF ELEMENTAL ANALYSIS

(75) Inventors: Luigi Ragaglia, Cassina de'Pecchi (IT); Giacinto Zilioli, Cernusco Sul Naviglio (IT); Franca Andreolini, Cornegliano Laudense (IT); Liliana Noemi Krotz, Lodi (IT)

(73) Assignee: Thermoquest Italia S.p.A., Radano (IT)

( * ) Notice: Subject to any disclaimer, the term of this patent is extended or adjusted under 35 U.S.C. 154(b) by 0 days.

(21) Appl. No.: 09/050,912

(22) Filed: Mar. 31, 1998

(65) Prior Publication Data

US 2001/0018218 A1 Aug. 30, 2001

(30) Foreign Application Priority Data

May 4, 1998 (IT) .......................................... MI98A0435

(51) Int. Cl.[7] .......................... G01N 30/12; G01N 31/12
(52) U.S. Cl. .......................... 436/160; 422/78; 422/79; 422/80; 436/43; 436/52; 436/106; 436/114; 436/115; 436/145; 436/155; 436/159; 436/161; 436/181
(58) Field of Search .................. 422/78–80; 436/20–24, 436/43, 52, 106, 114, 115, 145, 155, 159, 160, 181, 161

(56) References Cited

U.S. PATENT DOCUMENTS 3,784,359 A * 1/1974 Parth

FOREIGN PATENT DOCUMENTS

| EP | 0 586 969 A2 | 3/1994 |
| GB | 1170734 | * 11/1969 |
| GB | 2150691 A | 7/1985 |

OTHER PUBLICATIONS

Miller, C. D. Microchemical Journal 1966, 11, 366–375.*
Kainz, G. et al, Mikrochica Acta 1967, 714–720.*
Gel'man N. Talanta 1969, 16, 464–467.*
Fraisse, D. et al, Microchemical Journal 1977, 22, 109–130.*
Binkowski, J. et al, Chemia Analityczna 1984, 29, 471–481.*
Yamagata, M. et al, Nippon Dojo Hiryokgaku Zasshi 1988, 59, 308–311.*
Barrie, A. Spectroscopy 1989, 4, 42 and 44–52.*
Harris, D. et al, Communications in Soil Science and Plant Analysis 1989, 20, 935–947.*
Kuboyama, K. et al, Sankyo Kenkyusho Nenpo 1990, 42, 33–39.*
Farina, A. et al, Microchemical Journal 1991, 43, 181–190.*
Brookes, S. T. et al, Journal—Association of Official Analytical Chemists 1991, 74, 627–629.*

(List continued on next page.)

Primary Examiner—Arlen Soderquist
(74) Attorney, Agent, or Firm—Millen, White, Zelano & Branigan, P.C.

(57) ABSTRACT

Elemental analysis of a sample is carried out in an oxygen atmosphere in a combustion reactor and the volume of oxygen required for analysis is determined by means of the algorithm $$Q_o = \Delta(Q_c) \quad [1]$$

where $Q_o$ is the volume of oxygen required and $Q_c$ is the weight of the sample to be analyzed and $\Delta = Q_{o1}/Q_{c1}$ where $Q_{o1}$ is the volume of oxygen necessary for the combustion of a predetermined quantity $Q_{c1}$ of the sample to be analyzed, the volume of oxygen $Q_o$ is then fed in pulsed mode to the combustion reactor, by means of a flow detector.

8 Claims, 3 Drawing Sheets

OTHER PUBLICATIONS

Ray, P. K. et al, Journal of Mines, Metals & Fuels 1993, 41, 150–155.*
Pu, Q. J. Chem. Inf. Comput. Sci. 1993, 33,868–870.*
Barrie, A. et al, Fertilizer Research 1995, 42, 43–59.*
Barrie, A. et al, Nucl. Tech. Soil–Plant Stud. S. 1995, 29–61.*
Barrie, A. et al, Mass Spectrometry of Soils 1996, 1–46.*
W. Merz Talanta 1974, 21, 481–499.*
H. Trutnovsky Z. Anal. Chem. 1963, 198, 331–344.*
W. Merz Fresenius' Z. Anal. Chem, 1968, 237, 272–279.*
E. Pella et al. Mikrochim. Acta 1973, 697–719.*
W. Merz Int. Lab, 1974, 29–30, 32,34,36,38 & 40–41.*
G. Dugan Anal. Lett. 1977, 10, 639–657.*
I. J. Oita et al, Anal. Chem. 1980, 52, 1007–1008.*
W. J. Kirsten et al, Anal. Chim. Acta 1987, 196, 59–68.*
G. K. Buckee Monogr.–Eur. Brew. Conv. 1993, 20, 2–13.*
Kirsten et al. (1986) Analytical Chemistry Aug. No. 9 pp. 2109–2112.
Colombo et al. (1982) International Laboratory vol. 12 No. 7, pp. 76,78,80,82 & 84.

* cited by examiner

PROCESS AND DEVICE OF ELEMENTAL ANALYSIS

The present invention relates to a process and a device of elemental analysis of the Carbon, Hydrogen, Nitrogen, and Sulfur content by means of flash combustion in oxygen and for the analysis of the Oxygen content by means of pyrolysis.

Various processes for elemental analysis by means of "flash combustion" of the sample are known. This technique provides for the introduction of the sample into a heated reactor vessel in the presence of oxygen so as to cause substantially instantaneous combustion of the same; the gases released are then analyzed. Generally, the sample is housed in a tin (Sn) container.

One known process of analysis (used by LECO®-USA) provides for operation in a continuous flow of oxygen. The resulting gases are treated to ensure all combustion is complete and sent to a mixing tank where only a part is then analyzed. The main drawback of this solution is the large quantity of oxygen consumed; furthermore, the step of removal of a part of the combustion gases is a possible source of problems.

European Patent Application N. 0586969, In the name of the present applicant describes an elemental analysis process to determine the total nitrogen content. According to this document, the flash combustion is carried out in a flow of helium, with the necessary oxygen being supplied from a loop. The loop must be kept constantly full, with consequent consumption of oxygen; furthermore the quantity of sample which can be analyzed depends on the volume of the oxygen loop.

An aim of the present invention is to avoid the aforementioned drawbacks, and provide a process for elemental analysis which is flexible and inexpensive, which reduces the volume of oxygen consumed to a minimum, and which can be applied without problems to samples varying widely in weight and substance.

It also is an aim of this invention to provide a device to carry out the above process.

Namely, the present invention relates to a process for elemental analysis by means of flash combustion, characterized by comprising the following steps: determining the volume of oxygen required for the analysis of the sample by means of the following algorithm:

$$Q_o = \Delta(Q_c) \quad [1]$$

where:

$Q_o$ is the volume of oxygen required, $Q_c$ is the weight of the sample to be analyzed and $\Delta = Q_{o1}/Q_{c1}$ where $Q_{o1}$ is the volume of oxygen necessary for the combustion of a predetermined quantity $Q_{c1}$ of the sample to be analyzed;

pulse-feeding the said volume of oxygen $Q_o$ to the said combustion reactor from a source of oxygen, by means of a flow regulator.

According to a preferred aspect of the invention, the value $\Delta$ is determined experimentally for each type or class of sample in relation to their nature, and memorized in a means of retrieval and processing for use in the analysis.

According to a further aspect of the invention, the volume of oxygen required $Q_{o1}$ is determined by measuring the time $T_c$ required for the complete combustion of said predetermined quantity of sample $Q_{c1}$. The flow-rate P of the oxygen fed to combustion reactor is measured, and the said value $T_c$ is multiplied by the said value P.

The invention relates furthermore to a device for flash elemental analysis, comprising a combustion reactor, means for supplying a flow of inert carrier to the device, a source of oxygen and a feed line for feeding oxygen to said reactor, a flow regulator on said feed line of oxygen, and means of determining the volume of oxygen required for analysis of the sample by means of the following algorithm $$Q_o = \Delta(Q_c) \quad [1]$$

where $Q_o$ is the volume of oxygen required, $Q_c$ is the weight of the sample to be analyzed and $\Delta = Q_{o1}/Q_{c1}$, and where $Q_{o1}$ is the volume, known and measured, of oxygen necessary for the combustion of known quantity $Q_{c1}$ of the sample to be analyzed.

According to a preferential aspect of the invention, the device furthermore comprises a means of memorization and electronic processing in order to: memorize a plurality of constants $\Delta$ for a corresponding plurality of types of sample; memorize the algorithm [1]; receive the data related to the type and quantity of sample to be analyzed and calculate the said volume of oxygen $Q_o$ required for each analysis.

The invention has numerous advantages compared to the present state of the art. The advantages are of an economic, analytical and practical nature. The process of the invention allows the use of only that quantity of oxygen necessary to completely burn the sample, in slight excess. The daily consumption of oxygen for analyses has been found to be about one tenth of the consumption which would be used by traditional oxygen loop systems of analysis. A further advantage is that, as well as saving oxygen, there is also saving on reduced copper—necessary to reduce oxides—which now lasts longer. In practice it is possible to at least double the number of analyses obtained for the same quantity of reduced Cu used, compared to oxygen loop analysis.

The analytical advantages result from the greater efficiency of the copper which, not having to treat large quantities of analytical oxygen, remains unaltered over time.

From a practical point of view, the various $\Delta$ have been established experimentally for a large number of samples of diverse type and nature and are memorized in a processor in the production step of the device. At the moment of analysis, the operator is only required to set the type and the weight of sample to obtain automatic delivery of the quantity of oxygen necessary to burn the sample. Only where the type of sample to be analyzed is not among those in memory or where the nature of the sample is unknown, does the operator proceed to establish the $\Delta$ and memorize it.

The invention will now be described in more detail with reference to the attached drawings which are by way of example and not limiting, in which.

Figure 1:
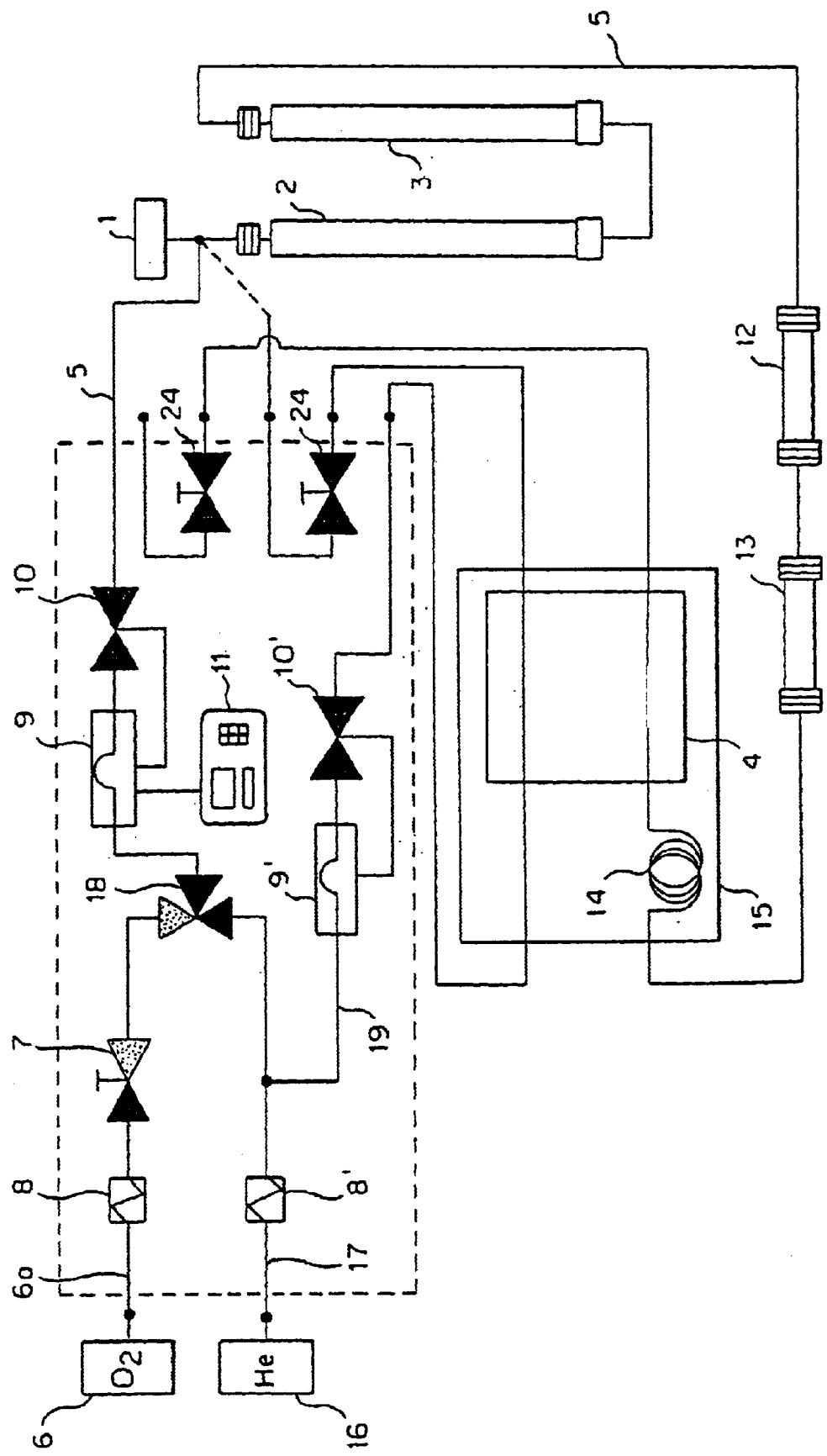
FIG. 1 is a layout of the device according to the invention prior to the introduction of the oxygen.

The device shown in FIG. 1 comprises a sampler 1 (known per se in the art), an oxidation reactor 2, a reduction reactor 3 and a thermo-conductivity detector (TCD) 4, connected to each other by means of a line 5. Line 5 upstream of is sampler 1 is connected to a source of oxygen 6 by means of line 6a and three-way valve 18. Beyond valve 18, between source of oxygen 6 and sampler 1 there are: a filter 8, an on/off valve 7, a flow detector 9 and a proportional valve 10 which is connected with flow detector 9.

Flow detector 9 is furthermore connected with a means of calculation 11, consisting of an electronic processor, which allows the volume of oxygen required for analysis of a sample to be determined as a function of both its weight and type of material. As will be described below, the volume of oxygen necessary is calculated by means of the algorithm $$Q_o = \Delta(Q_c) \quad [1]$$

where $Q_o$ is the volume of oxygen required and $Q_c$ is the weight (known and measured) of the sample to be analyzed. $\Delta$ is a constant which depends on the type of material and which is determined experimentally, in advance.

Furthermore, the means of calculation 11 allow: a plurality of constants $\Delta$ to be memorized for a corresponding plurality of samples; the algorithm [1] to be memorized, the data related to the type and weight of the samples before analysis to be input, and the volume of oxygen required $Q_o$ for analysis of each single sample to be calculated.

Downstream of reduction reactor 3 there is a filter for $CO_2$ 12 and a filter for $H_2O$ 13 (optional), a column 14 and TCD detector 4. The column and detector are housed in an oven 15. The material with which the column is packed depends on the type of analysis to be done; e.g. Porapack® is used for a CHN analysis; molecular sieves are used for analysis of oxygen, and activated carbon is used for analysis of N alone.

The device, or analysis apparatus, further comprises 8 source of helium 16 connected by line 17 to three-way valve 18 and via the same to analysis line 5. A filter 8' similar to filter 8 is located on line 17 upstream of valve 18. Line 17 has a branch 19 which extends through detector 4 and acts as a reference line. The flow of helium along this line is controlled by flow regulator 9' and by proportional valve 10' and at the outlet from line 19 is sent to sampler 1 to wash over the sample in the sampler.

Figure 2:
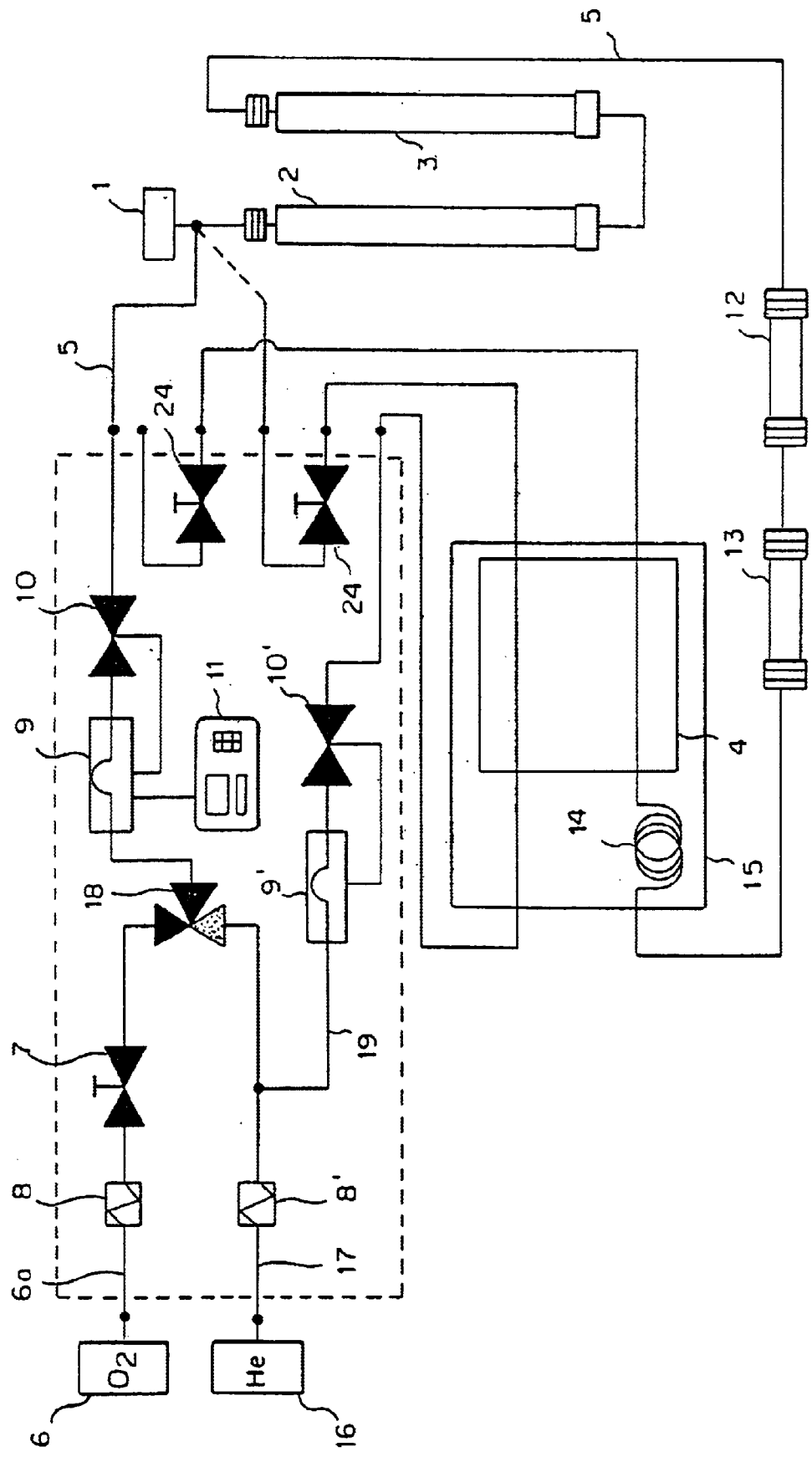
FIG. 2 is a layout of the device of FIG. 1, during the oxygen introduction step.

The two configurations of FIGS. 1 and 2 are structurally identical and show the "PreRun" step in FIG. 1 i.e. the step in which He is fed to line 5; valve 7 is closed and three-way valve 18 connects the only source of source of helium 16 with analysis line 5. During the oxygen introduction step (FIG. 2) valve 7 is open and valve 18 connects the source of oxygen 6 with line 5, only.

Lines 5 and 19 are furthermore provided with valves 24 close to their extremities; valves 24 are used to check the gas-seal of the system as described below.

Figure 3:
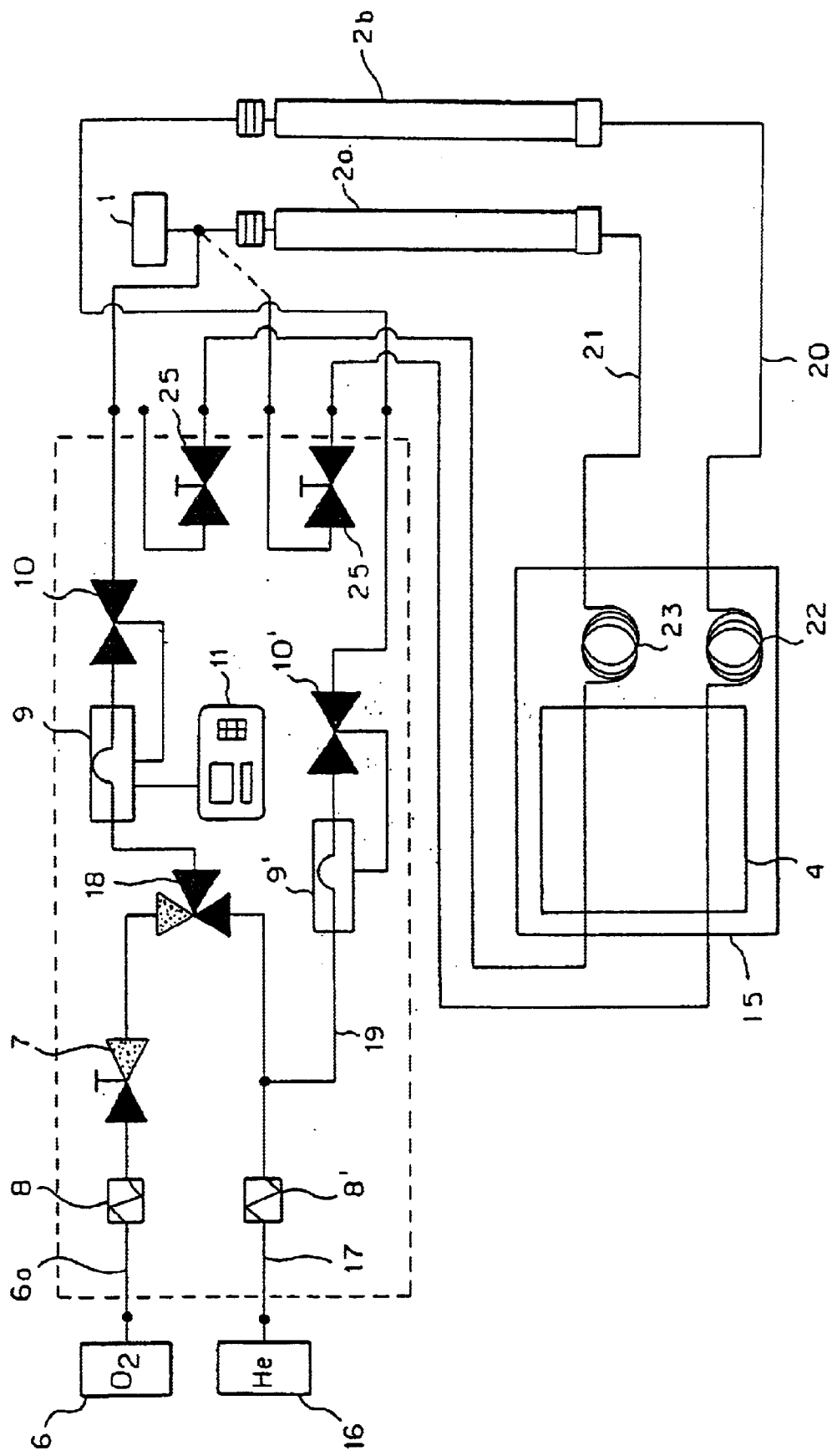
FIG. 3 is a layout of an embodiment for CHNS-O analysis.

FIG. 3 shows an embodiment which allows to switch from analysis of CHNS to analysis of oxygen in a short time without substantial modifications to the instrument. In this device there are two reactors 2a and 2b, the first for analysis of CHNS and the second for the analysis of oxygen alone.

Two lines 20 and 21 extend from the two reactors to two columns 22 and 23 respectively, in oven 15, so as to give two independent analytical circuits. It is only necessary to shift sampler 1 (and line 5 connected to it) from one reactor to the other to switch from one type of analysis to the other. In one possible embodiment, an automatic sampler for CHNS on reactor 2a is combined with a manual sampler on reactor 2b for the determination of oxygen. FIG. 3 shows the "PreRun" configuration for the determination of CHNS. Two valves 25 with similar function to valves 24 of FIGS. 1 and 2 are located at the end of lines 20 and 21.

The device according to the invention operates in the following way:

the value $\Delta$ is initially determined experimentally for a series of different types of sample, e.g. cereals, cheese, meat, etc. Each $\Delta$ refers to a type of sample and is inserted into the memory of the means of calculation 11, i.e. the computer which controls the instrument.

The value $\Delta$ is calculated as follows: $\Delta = Q_{o1}/Q_{c1}$ where $Q_{o1}$ is the volume of oxygen necessary (and measured experimentally) for the complete combustion of the (known) quantity of sample $Q_{c1}$.

$Q_{o1}$ is obtained from the relation $$Q_{o1} = T_c P$$

where $T_c$ is the time necessary (measured experimentally) for combustion of the quantity of sample $Q_{c1}$ and P is the flow-rate of oxygen sent to combustion reactor 2 or 2a, measured in cc/min. In other words, the time $T_c$ necessary for the combustion of the predetermined quantity of sample $Q_{c1}$ is measured, then flow-rate P of the oxygen fed to the said combustion reactor is measured, and eventually said value $T_c$ is multiplied by the value of P.

To measure the time $T_c$ a control cycle is carried out first with just the container in Sn: the container is placed in the reactor 2 and the oxygen is then fed in. The time necessary for the oxygen to arrive at the reactor 2 is measured, observing the flash of the container when the oxygen reaches the reactor.

At this point the quantity $Q_{c1}$ of the chosen sample is weighed, e.g. 100 mg, and placed in the container and the maximum flow of oxygen is set, e.g. 300 cc/min for 1 minute. Knowing how long it takes for the oxygen to reach the reactor, the sample is introduced into the reactor just before or at the moment in which the oxygen reaches the reactor and the combustion time Tc is measured by observing the point at which the burning is extinguished.

Assuming a combustion time Tc of 0.5 minutes, the calculation of the volume of oxygen $Q_{o1}$ necessary for the sample $Q_{c1}$ is:

$$(0.5 \text{ min}) \times (300 \text{ cc/min}) = 150 \text{ cc} = Q_{o1}.$$

And therefore $$\Delta = Q_{o1}/Q_{c1} = 150 \text{ cc}/100 \text{ mg} = 1.5 \text{ cc/mg}$$

This value of $\Delta$ is used for all the classes of the related type of samples and is used to determine the volume of oxygen necessary for successive samples of the same type; e.g. if the sample to be analyzed weighs 200 mg, the volume of oxygen is $Q_{o1} = \Delta Q_c = (1.5 \text{ cc/mg}) \times 200 \text{ mg} = 300 \text{ cc}$.

As mentioned above, $\Delta$ values for a large quantity of types of product to be analyzed are already established and inserted into the memory of the processor 11 in the production step of the device of the invention. When the operator carries out the analysis of a sample, initially he sets the type of product to be analyzed, then the weight of the sample (or samples to be analyzed in sequence) is also set into processor 11. The processor identifies the $\Delta$ characteristic of the type of product and calculates the individual quantity of oxygen necessary for analysis of each sample according to the algorithm $$Q_o = Q_c \quad [1]$$

as disclosed above.

During the step preceding combustion of the sample (PreRun) helium is fed to the inlet of line 17 at a working pressure of 350–400 kPa, it flows along line 5 and is controlled by flow regulator 9 at a flow-rate between 0 and 300 cc/min according to the analytical configuration. The flow of helium passes through reactors 2 and 3, filters 12 and 13, if present, column 14 and detector 4. Similarly, helium flows along line 19 where it is controlled by flow regulator 9' between 0 and 300 cc/min (generally at 70–80 cc/min) and then flows through detector 4 and washes over sampler 1.

During this step (PreRun) valve 7 is closed and the oxygen is not fed to the device.

When the operator sends the signal to begin the analysis cycle, valve 7 opens and valve 18 is set for feeding only oxygen to analysis line 5. The quantity of oxygen necessary for each analysis is determined by means of calculation 11 as previously described and is controlled by means of flow regulator 9 and proportional valve 10. The sample is introduced some seconds after the signal to begin the analysis cycle Is given; the operator can set the time of introduction of the sample.

The gases generated by the combustion of the sample are treated in a way already known in the art. At the end of the oxygen introduction step the valves are switched again to the position for feeding helium, as described above.

The valves 24 and 25 are used to check that the pneumatic system is gas-tight. To do this, helium is fed to lines 5 and 19, or 19 and 20 or 21, and valves 24 and 25 are closed; if the system is gas-tight, the flow of helium measured by flow detector 9' falls substantially to zero within a pre-determined time; where it does not, there are leaks of some kind in the pneumatic system.

A series of analysis of the nitrogen content of samples was carried out to check the validity of the process according to the present invention.

The samples used are Standard Reference Material #1547 (peach leaves) obtainable from National Institute of Standard & Technology—US Department of Commerce. The certified value of nitrogen content of these samples is 2,94% ±0,12.

After obtaining the Δ, seven analysis of samples with increasing weight were carried out; the results are set out in the following table:

TABLE 1

| sample weight (g) | % nitrogen |
|---|---|
| 0,102 | 2,94 |
| 0,156 | 2,94 |
| 0,204 | 2,97 |
| 0,253 | 2,96 |
| 0,303 | 2,95 |
| 0,351 | 2,97 |
| 0,402 | 2,97 |

What is claimed is:

1. A process for providing automatically only a required amount of oxygen for elemental analysis by complete flash combustion of samples in an oxygen atmosphere in a combustion reactor normally fed with a flow of inert carrier gas wherein oxygen consumption is minimized, comprising:
experimentally determining a Δ constant for each type of sample to be analysed according to the following formula:

$$\Delta = Q_{o1}/Q_{C1}$$

where:
$Q_{c1}$ is a predetermined quantity of a sample of the same type of the sample to be analyzed, $Q_{01}$ is the volume of oxygen required for the combustion of predetermined quantity $Q_{c1}$ of a sample of the same type as the sample to be analyzed, and
Δ is a constant for the type of sample to be analyzed and storing the constant Δ for each sample as data in an electronic database inputting the type and quantity of a sample into a processor connected to the electronic data base to compute a value $Q_o$ for the volume of the the oxygen required for the analysis of that sample, by using the following formula stored in the electronic database:

$$Q_o = \Delta(Q_c)$$

where:
$Q_o$ is the volume of oxygen required for combustion,
$Q_c$ is the weight of the sample to be analysed,
Δ is the constant for the sample type to be analysed,
switching off the flow of inert carrier gas to the combustion reactor;
supplying the required amount of oxygen by connecting the combustion reactor to a source of oxygen by means of a mass flow regulator and using the same oxygen flow rate used for the determination of $O_{O1}$;
restoring the flow of inert carrier gas to the combustion reactor at the end of the oxygen introduction step;
thereby feeding in pulsed mode the required volume of oxygen $Q_O$ to said combustion reactor automatically from a source of oxygen through a valve operated by a calculating device via a flow detector.

2. A process according to claim 1, wherein $Q_{O1}$ is calculated by: measuring the time $T_C$ necessary for the combustion of the pre-determined quantity of sample $Q_{C1}$, measuring the flow-rate P of the oxygen fed to the combustion reactor, and multiplying $T_C$ by P.

3. A process according to claim 2, wherein said flow of oxygen is constant during the combustion step of the sample.

4. A process according to claim 1, wherein a flow of an inert carrier gas is fed to the analysis device before and after the pulsed oxygen, and a flow of said carrier is fed to a reference branch of the combustion chamber.

5. A device for providing automatically only a required amount of oxygen for a flash elemental analysis of a sample wherein oxygen consumption is minimized, comprising:
a combustion reactor,
a supply of a flow of an inert carrier gas to the device,
an oxygen feeding system comprising:
a source of oxygen,
a feed line from the source of oxygen to the combustion reactor,
a pulse-feeder for pulse-feeding oxygen to the reactor,
a mass flow regulator on said feed line of oxygen, and
valve means for disconnecting the combustion reactor from the flow of inert carrier gas, and
a calculating device connected to the oxygen feeding system for determining automatically a Δ constant for each type of sample to be analyzed according to the following equation:

Δ is $Q_{o1}/Q_{C1}$ where:
$Q_{C1}$ is a known quantity of sample; and
$Q_{O1}$ is the only volume of oxygen necessary for complete combustion of a known quantity $Q_{C1}$ of the sample to be analyzed and for computing automatically the volume of oxygen required and to be fed for analysis of the sample by using the same oxygen flow rate used for the determination of $Q_{o1}$ and using the following equation:

$$Q_O = \Delta(Q_C) \tag{1}$$

$Q_O$ is the volume of oxygen required, $Q_c$ is the weight of the sample to be analyzed, where:

$\Delta$ is the constant for the sample type to be analysed.

6. A device according to claim 5, further comprising an electronic device for:
   containing a plurality of constants $\Delta$ for a corresponding plurality of types of samples;
   containing formula $Q_o = \Delta (Q_c)$ and being capable of receiving data related to a type and quantity of sample to be analyzed for calculating said volume of oxygen $Q_o$ required for a predetermined quantity of a sample of the same type.

7. A device according to claim 6 wherein said flow detector is connected with a proportional valve and with said electronic device.

8. A device according to claim 6, further comprising a feed for feeding said inert carrier gas to said combustion reactor and to a reference line dedicated to the carrier gas alone.

* * * * *

UNITED STATES PATENT AND TRADEMARK OFFICE
CERTIFICATE OF CORRECTION

PATENT NO. : 6,653,143 B2
DATED : November 25, 2003
INVENTOR(S) : Luigi Ragaglia et al.

It is certified that error appears in the above-identified patent and that said Letters Patent is hereby corrected as shown below:

Title page,
Item [73], Assignee, reads "Thermoquest" should read -- ThermoQuest --

Column 6,
Line 8, reads "$\Delta$is" should read -- $\Delta$ is --
Line 16, reads "$O_{O1}$" should read -- $Q_{01}$ --

Signed and Sealed this

Twenty-fifth Day of January, 2005

JON W. DUDAS
*Director of the United States Patent and Trademark Office*